(12) United States Patent
Kabumoto et al.

(10) Patent No.: US 8,019,040 B2
(45) Date of Patent: Sep. 13, 2011

(54) X-RAY INSPECTION DEVICE AND PRODUCTION SYSTEM

(75) Inventors: Takashi Kabumoto, Shiga (JP); Osamu Hirose, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 126 days.

(21) Appl. No.: 12/530,303

(22) PCT Filed: Mar. 7, 2008

(86) PCT No.: PCT/JP2008/054185
§ 371 (c)(1),
(2), (4) Date: Sep. 8, 2009

(87) PCT Pub. No.: WO2008/111522
PCT Pub. Date: Sep. 18, 2008

(65) Prior Publication Data
US 2010/0135459 A1    Jun. 3, 2010

(30) Foreign Application Priority Data
Mar. 12, 2007  (JP) .................................. 2007-061443

(51) Int. Cl.
*G01N 23/04* (2006.01)
(52) U.S. Cl. .......................................... 378/57; 378/58
(58) Field of Classification Search .................... 378/57, 378/58, 207
See application file for complete search history.

(56) References Cited

U.S. PATENT DOCUMENTS

| | | | |
|---|---|---|---|
| 6,023,497 A | * | 2/2000 | Takahashi et al. ............. 378/57 |
| 2001/0014138 A1 | * | 8/2001 | Knigge et al. .................. 378/57 |
| 2008/0240578 A1 | * | 10/2008 | Gudmundson et al. ....... 382/218 |

FOREIGN PATENT DOCUMENTS

| | | |
|---|---|---|
| JP | S62-225935 A | 10/1987 |
| JP | 2003-028663 A | 1/2003 |
| JP | 2005-003481 A | 1/2005 |
| JP | 2006-145380 A | 6/2006 |
| JP | 2006-322750 A | 11/2006 |

OTHER PUBLICATIONS

English language translation of JP 2006-322750 A.*

* cited by examiner

*Primary Examiner* — Hoon Song
*Assistant Examiner* — Mona M Sanei
(74) *Attorney, Agent, or Firm* — Global IP Counselors, LLP (57) ABSTRACT

An X-ray inspection device includes a conveying unit, an identification part, and an operation control part. The X-ray inspection device irradiates articles with X-rays while the article is being conveyed, and the article is inspected. The conveying unit is configured and arranged to convey the article. The identification part is configured and arranged to identify whether the article is a test piece or an end product. The operation control part is configured to set operation of the X-ray inspection device to a normal mode in which the article is determined to be defective or not defective when the article has been identified as an end product by the identification part, and to a test mode in which a state of the device is assessed when the article has been identified as a test piece by the identification part.

6 Claims, 6 Drawing Sheets

X-RAY INSPECTION DEVICE AND PRODUCTION SYSTEM

CROSS-REFERENCE TO RELATED APPLICATIONS

This application claims priority to Japanese Patent Application No. 2007-061443, filed on Mar. 12, 2007. The entire disclosure of Japanese Patent Application No. 2007-061443 is hereby incorporated herein by reference.

TECHNICAL FIELD

The present invention relates to an X-ray inspection device, and to a production system that includes the X-ray inspection device.

BACKGROUND ART

X-ray inspection devices have conventionally been used to inspect commercial products in order to avoid shipping ones contaminated with foreign matter. In the X-ray inspection devices, an X-ray detection diagnostic test is carried out when the device is powered on. However, since the X-ray source in the X-ray inspection device will deteriorate over time, a proposed X-ray inspection device has a test mode, in addition to the diagnostic test carried out when the device is powered on, wherein the state of the device is assessed by inspecting a test piece including the foreign matter or the like, and detecting the test piece. (See Japanese Laid-Open Patent Application 2005-3481)

DISCLOSURE OF THE INVENTION

However, in the conventional X-ray inspection devices, the product production line must be stopped, in order to switch the devices to the test mode. Consequently, the production efficiency is severely reduced due to the need to stop the production of the products.

Therefore, one object of the present invention is to provide an X-ray inspection device and a production system that includes the X-ray inspection device in which the state of the X-ray inspection device can be assessed without stopping the production of the products.

In order to achieve the above-mentioned object, an X-ray inspection device according to the first aspect is adapted to irradiate an article with X rays and to inspect the article while the article is being conveyed. The X-ray inspection device includes a conveying unit, an identification part, and an operation control part. The conveying unit is configured and arranged to convey the article. The identification part is configured and arranged to identify whether the article is a test piece or an end product. The operation control part is configured to set operation of the X-ray inspection device to a normal mode in which the article is determined to be defective or not defective when the article has been identified as an end product by the identification part, and to a test mode in which a state of the device is assessed when the article has been identified as a test piece by the identification part.

According to the first aspect, it is possible to identify an end product from a test piece by using the identification part. Therefore, it is possible to automatically shift to the test mode by inserting a test piece, even without stopping the flow of products.

In the X-ray inspection device as described above, the identification part is preferably configured and arranged to compare a transmission image of the X-rays irradiated onto the article with a prescribed identification reference to identify whether the article is a test piece or an end product.

Accordingly, the identification is carried out by using the X-ray transmission image. Therefore, the identification can be carried out simply by adding software, and it is not necessary to provide a hardware device. Accordingly, no concerns of a large-scale cost increase will arise.

The X-ray inspection device as described above preferably further includes a first storage part configured and arranged to store the prescribed identification reference. The identification part is preferably configured and arranged to identify whether the article is a test piece or an end product based on the transmission image of the X-rays irradiated onto the article and the prescribed identification reference stored in the first storage part.

According to the present aspect, it is possible to automatically determine the presence of a test piece by providing a reference used for performing the identification.

The X-ray inspection device as described above preferably further includes a registration part configured and arranged to execute a registration mode in which the prescribed identification reference is obtained from a reference transmission image of the X-rays with which a test piece is irradiated, and prescribed identification reference is stored in the first storage part.

According to the present aspect, the test piece can be readily registered using the registration mode.

The X-ray inspection device as described above preferably further includes a second storage part configured and arranged to store a threshold value corresponding to foreign matter provided to the test piece in the registration mode, and a device checking part configured and arranged to assess the state of the device based on the threshold value stored in the second storage part and the transmission image of the X-rays irradiated onto the article identified as a test piece by the identification part.

According to the present aspect, threshold values corresponding to different varieties of foreign matter are stored in the second storage part, making it possible to set a threshold value corresponding to the type of foreign matter. Therefore, the device can be tested for a variety of foreign matter, making it possible to check the device more accurately.

In the X-ray inspection device as described above, the identification part is preferably configured and arranged to identify whether the article is a test piece or an end product based on a timing at which the article is conveyed.

According to the present aspect, the test piece can be automatically inserted on the basis of the timing at which the articles are conveyed, making software for the X-ray inspection device simpler to develop.

A production system according to a second aspect includes the X-ray inspection device described above, and a production machine disposed on an upstream side of the X-ray inspection device. The test piece is preferably introduced in the production machine.

According to the present aspect, the test piece is more readily inserted.

According to the X-ray inspection device as described above, it is possible to identify an article from a test piece using identification part. Accordingly, it is possible to automatically shift to a test mode by inserting a test piece through, even without halting the flow of the articles.

BEST MODE FOR CARRYING OUT THE INVENTION

Embodiments of the present invention will be described below with reference to the drawings.

Embodiment 1

FIGS. 1 through 4 show Embodiment 1.

Overall Configuration

Figure 1:
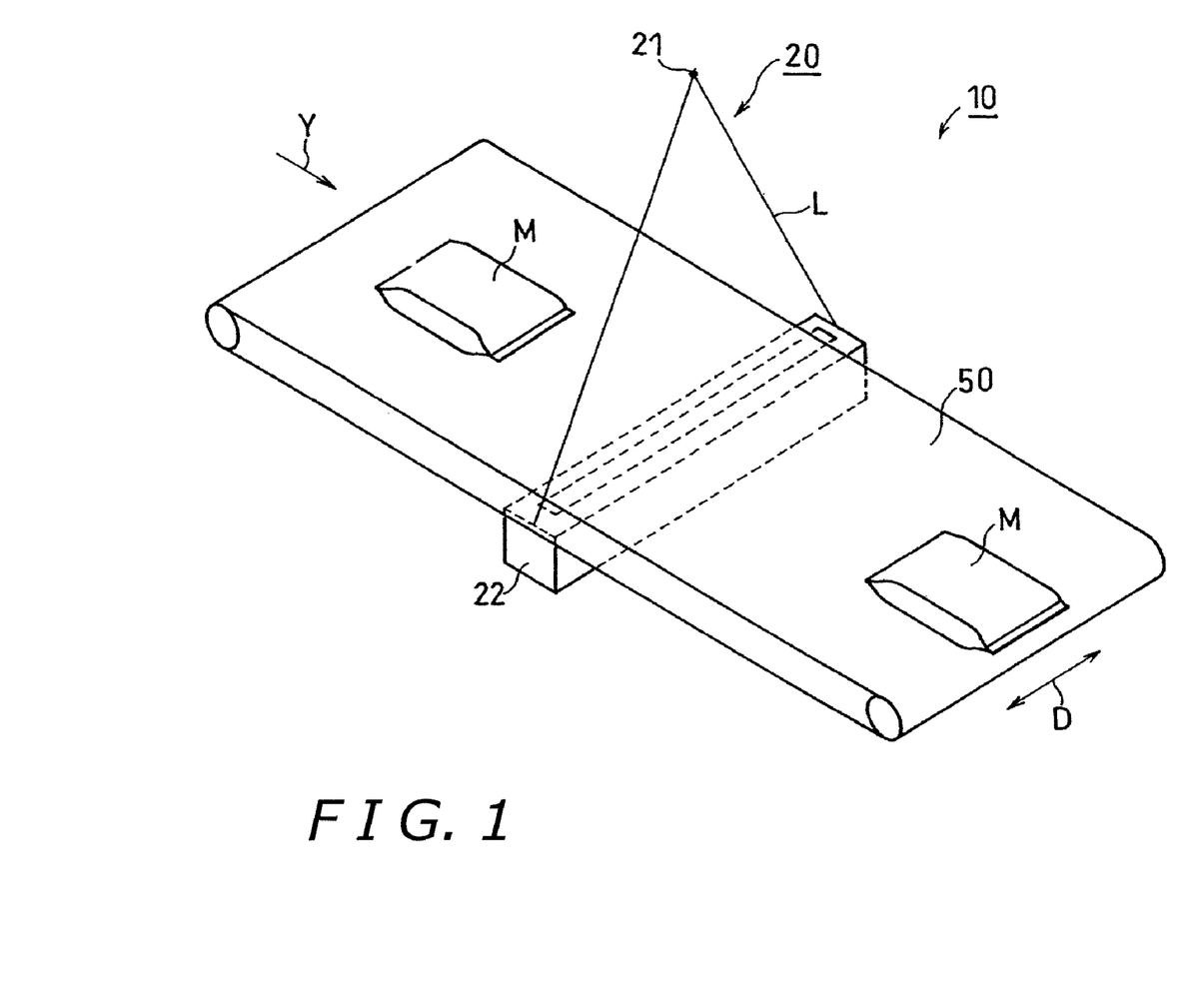
FIG. 1 is a schematic perspective view showing an X-ray inspection device according to an embodiment of the present invention.

As shown in FIG. 1, an X-ray inspection device 10 for inspecting articles using X-rays includes a conveyor (as an example of a conveying unit) 50 and an optical system 20. The optical system 20 includes an X-ray source 21 and a line sensor 22. The X-ray source 21 generates X-rays L, and the line sensor 22 is irradiated with the X-rays L.

The X-ray source 21 irradiates the X-rays L onto products M that are conveyed on the conveyor 50. The line sensor 22 is disposed beneath the conveyor 50 along a width direction D, which is substantially perpendicular to a conveying direction Y of the products M. The line sensor 22 detects the X-rays L that have passed through the products M.

Figure 2A:
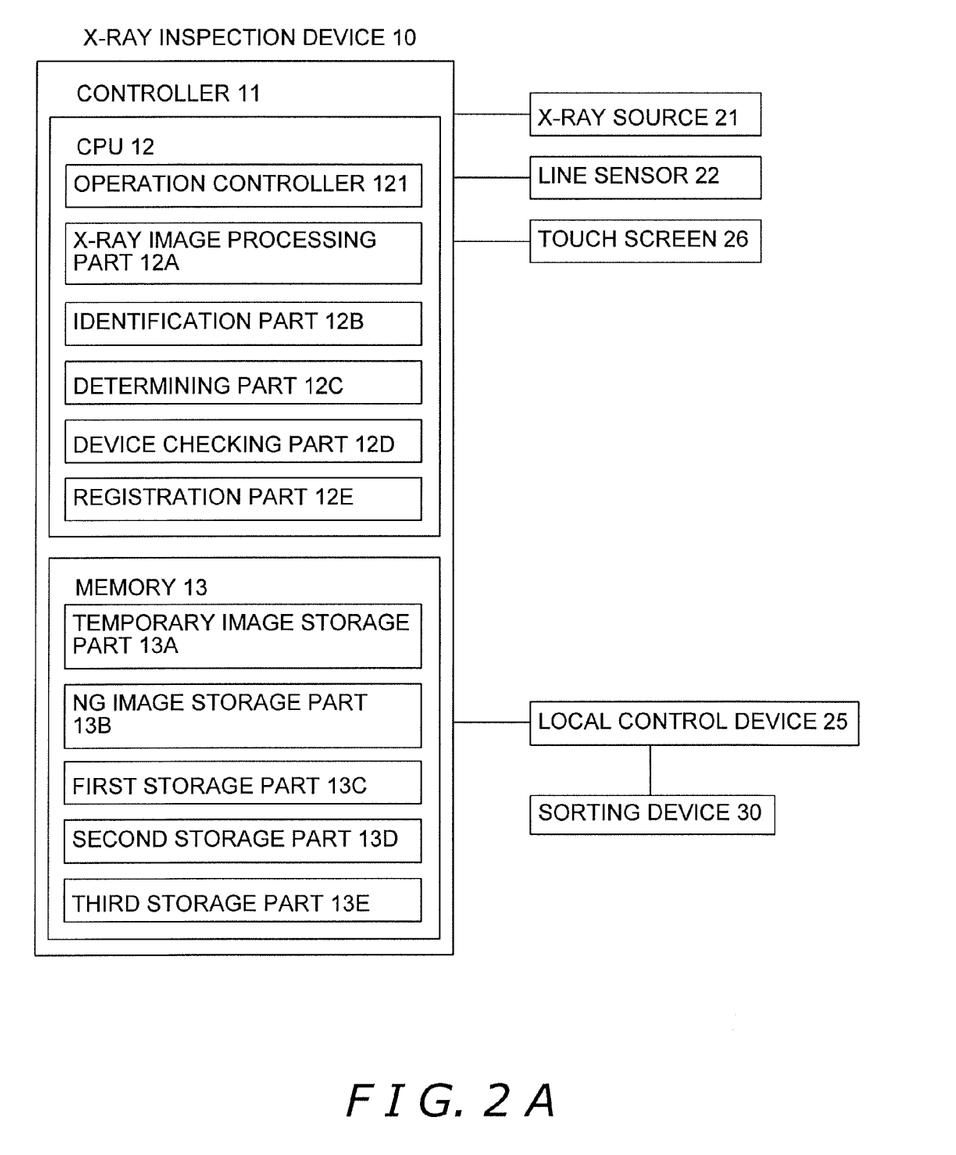
FIG. 2A is a schematic block diagram showing the X-ray inspection device and a sorting device.
Figure 2B:
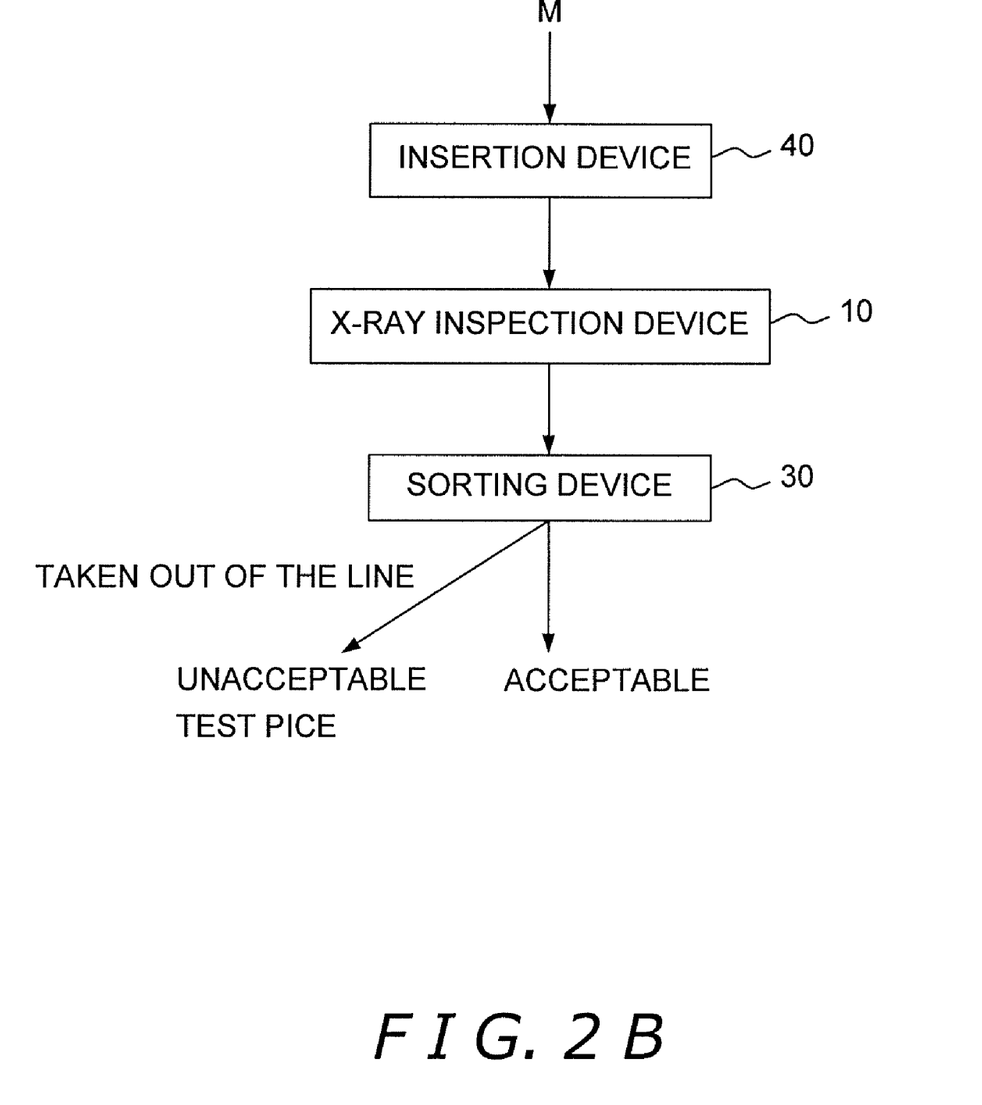
FIG. 2B is a schematic block diagram showing the flow of articles.

As shown in FIG. 2B, a sorting device 30 is provided downstream from the X-ray inspection device 10. The X-ray inspection device 10 detects the presence of foreign material or other errors, and any end product M regarded as a failure or test piece P (FIG. 4) is removed from the production line by the sorting device 30.

Test Piece P

Figure 4A:
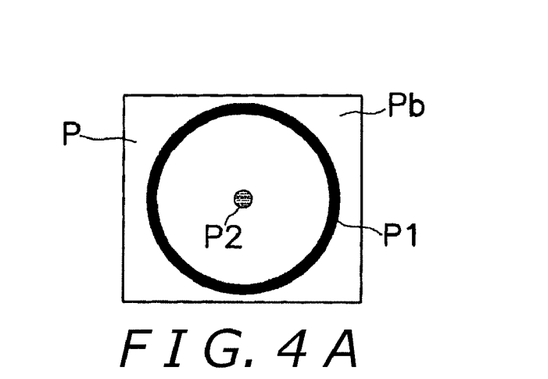
FIGS. 4A through 4E are schematic plan views showing examples of the test pieces.

The test piece P shown in FIG. 4A is introduced to the conveyor 50 at an appropriate timing, and conveyed. The test piece P is used to assess the state of the X-ray inspection device 10. For example, as shown in FIG. 4A, an annular marker P1 is attached onto a square resin plate Pb, and test foreign matter P2 is attached in the center of the circular region inside the marker P1.

The marker P1 is formed using, e.g., a thick metal plate or metal wire so that an image processing (as described below) can be readily executed as a result of the X-ray inspection image of the marker P1 captured by the line sensor 22 (FIG. 1) being darker than the darkest portions of the whole image of the products M. The test foreign matter P2 is formed using a metal foil or glass that is likely to contaminate the products M.

Configuration Of X-Ray Inspection Device

As shown in FIG. 2A, the X-ray inspection device 10 has a controller 11 including, e.g., a microcomputer. The X-ray source 21, the line sensor 22, a local control device 25, a touch screen 26, and the like are each connected to the controller 11 via interfaces (not shown).

The local control device 25 controls the operation of the conveyor 50 and the movement of the sorting device 30 and other components.

The touch screen 26 is used to display X-ray transmission images and a variety of other information on a liquid crystal screen or other display screen, and to carry out input and setting operations by touching a portion of the display.

Controller 11

The controller 11 includes a CPU 12 and a memory (storage part) 13.

The CPU 12 includes an operation controller 121 (an example of an operation control part) for operating the X-ray inspection device 10 in a normal mode, a test mode, and a registration mode.

The normal mode is a mode wherein an article being conveyed to the X-ray inspection device 10, and determined to be an end product M, is subjected to a pass-fail assessment as the end product M.

The test mode is a mode for assessing the state of the X-ray inspection device 10 when an article being conveyed to the X-ray inspection device 10 has been determined to be a test piece P.

The registration mode is a mode for storing a reference (including X-ray transmission image) used to identify the test piece P used in the test mode.

Memory 13

The memory 13 includes an temporary image storage part 13A, an NG image storage part 13B, a first storage part 13C, a second storage part 13D, and a third storage part 13E.

Figure 3:
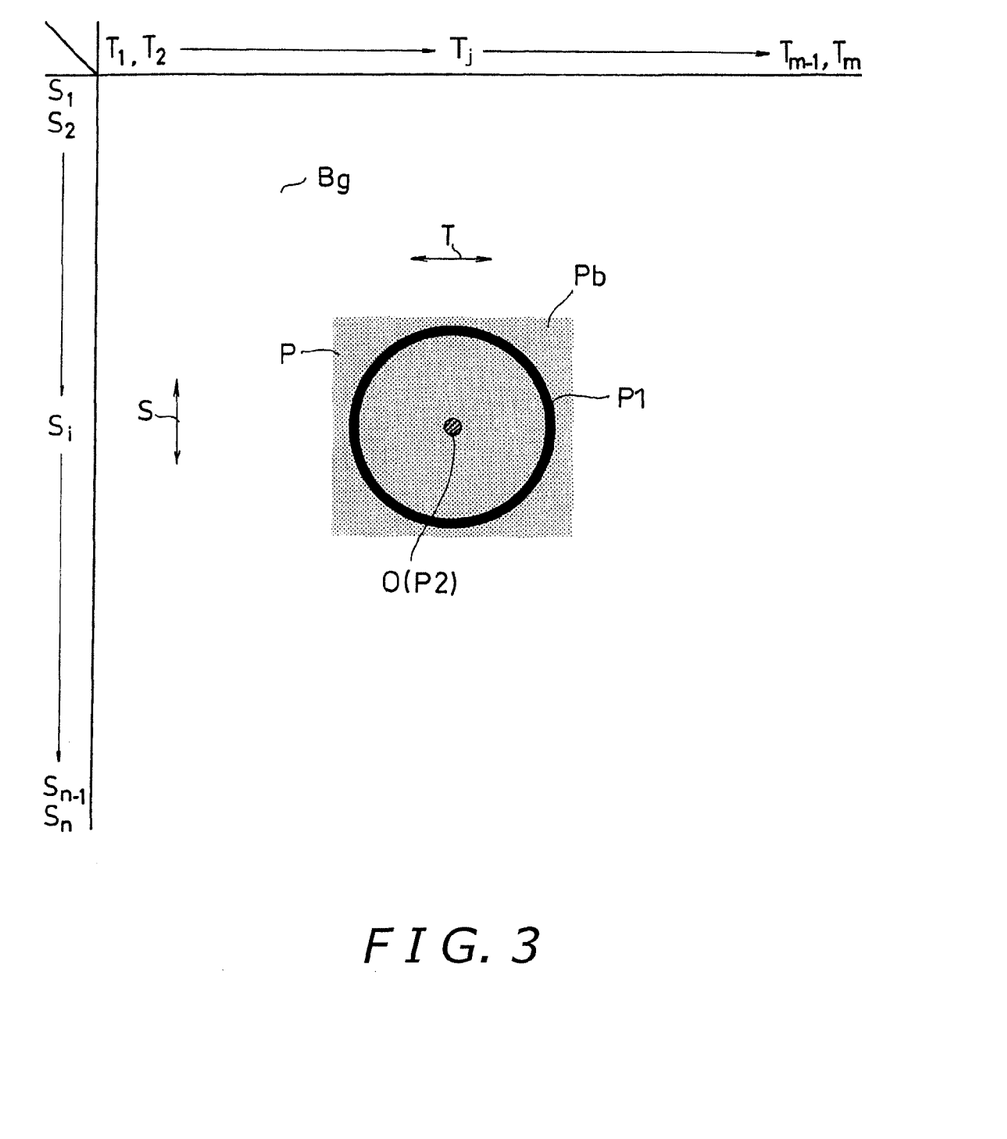
FIG. 3 is a schematic plan view showing an X-ray transmission image of a test piece.

The temporary image storage part 13A temporarily stores an X-ray transmission image, which is configured from an imaging signal from the line sensor 22, as shown in FIG. 3.

The NG image storage part 13B stores an X-ray transmission image of an end product M and the like that has been rejected by the determining part 12C.

The first storage part 13C stores the identification reference including a prescribed first threshold value and the shape of the marker P1, which are obtained on the basis of the X-ray transmission image of the test piece P captured by the line sensor 22 in the registration mode. The identification reference is used to identify the products M from the test piece P.

The second storage part 13D stores a second threshold value for assessing whether a prescribed type of foreign matter is present in the X-ray transmission image of the test piece P.

The third storage part 13E stores a third threshold value for determining whether foreign matter is included in the X-ray transmission image of an end product M.

CPU 12

In addition to the operation controller 121, the CPU 12 includes, an X-ray image processing part 12A, an identification part 12B, a determining part 12C, a device checking part 12D, and a registration part 12E and the like.

X-Ray Image Processing Part 12A

The X-ray image processing part 12A continually processes outputs from the line sensor 22 in the order received, on the basis of a timing at which the articles shown in FIG. 1 are conveyed on the conveyor 50. As a result, the x-ray image processing part 12A creates an X-ray transmission image shown in FIG. 3 that has a brightness distribution that corresponds to the amount of transmitted X-rays. In FIG. 3, the lightly dotted region indicates the resin portion of the test piece P, the region with diagonal lines indicates the test foreign matter P2, and the solid region indicates the marker P1.

X-Ray Transmission Image

The line sensor 22 (FIG. 1) is formed from multiple detector elements Si (i=a natural number from 1 to n), wherein n detector elements are arranged in a substantially linear fashion. The X-ray transmission image is an image that is constituted by a plurality of pixels, each of which corresponds to the amount of transmitted X-rays detected by each of the detector elements Si and recorded along a time-line over a prescribed period of time (Tm–T1). Accordingly, the X-ray transmission image is expressed on a coordinate system (Si, Tj)(j=a natural number from 1 to m) having the detector elements Si and the times Tj.

In the X-ray transmission image, a background Bg is brightly displayed, and the portions where the article is present are displayed darker according to the amount of transmitted X-rays. In the X-ray transmission image of the test piece P shown in FIG. 3, for example, the lightly dotted portion of the resin plate Pb is faintly displayed, while the portion of the marker P1 is displayed most darkly. The portion of the test foreign matter P2 shown by the slashed lines in FIG. 3 is darker than the resin plate Pb and lighter than the marker P1, according to the test foreign matter P2. A value that is slightly greater than the amount (the detection value) of X-rays that pass through the portion of the marker P1 is set as the first threshold value.

Identification Part 12B

The identification part 12B shown in FIG. 2A determines whether the article being conveyed on the conveyor 50 (FIG. 1) is an end product M or a test piece P, on the basis of the X-ray transmission image of the article, by comparing the transmission image (FIG. 3) of the X-rays irradiated to the article with the identification reference retrieved from the first storage part 13C.

The identification part 12B retrieves the first threshold value and shape of the marker P1 from the first storage part 13C, and identifies the end product M from the test piece P by determining whether the portions in the X-ray transmission image of the article that exceed the first threshold value is matched to the shape of the marker P1 retrieved from the first storage part 13C.

The article is determined to be an test piece P in the case that the identification part 12B determines that the marker P1, which corresponds to the shape, is present in the portions of the X-ray transmission image that exceed the first threshold value. When the portions do not correspond to the shape, the article is determined to be an end product M.

Method For Identifying End Product M From Test Piece P

Template matching, pattern matching, and a variety of other known image matching methods can be used as the method for identifying whether the portions of the X-ray transmission image that exceed the first threshold value match the shape retrieved from the first storage part 13C. These image matching methods involve comparing the portions of the X-ray transmission image that exceed the first threshold value with the shape, based on the area and the boundary length of the marker P1 portion in the binarized X-ray transmission image, and other characteristics.

A pattern matching scheme will be briefly described below as an example of the image matching.

In the first storage part 13C, data about a shape of the marker P1, including a binarized image of the test piece P (referred to as "registration image" hereinbelow), is stored in advance, the shape being the shape of portions in the X-ray transmission image of the test piece P that exceed the first threshold value extracted from the image in a registration mode (described below) in which the test piece P is registered.

The identification part 12B binarizes the X-ray transmission image of the article, using the first threshold value as a reference; and searches in pixel units for portions in the binaraized image which matches the registration image, the binaraized image being defined by a combination of the element direction S and the time-line direction T. As a result, the identification part 12B determines the position of the optimally-matched area between the registration image and portions in the binaraized image that exceed the first threshold value.

In the optimally-matched area, the number of pixels in which there is no matching between the registration image and the portions in the binaraized image that exceed the first threshold value is counted to determine the difference between the two images; and the article is identified as the end product M when the difference falls below or exceeds a prescribed range. When the difference is within the prescribed range, the article is identified as the test piece P.

Figure 4B:
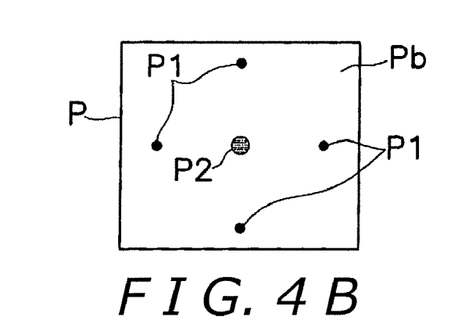
Figure 4C:
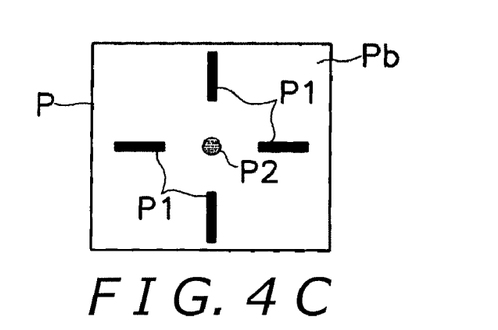

Unlike the markers P1 shown in FIGS. 4B and C, the marker P1 in FIG. 4A has an annular shape, that is rotational symmetry shape, when the identification process is carried out by the identification part 12B. Accordingly, it is not necessary to rotate and compare the registration image; therefore, image matching can be carried out even more efficiently.

In cases where the identification part 12B identifies the article as the end product M, the CPU 12 is set to the normal mode. In cases where the identification part 12B identifies the article as the test piece P, the CPU 12 is set to the test mode.

Determining Part 12C

In the normal mode, the determining part 12C determines whether foreign matter contamination has occurred, on the basis of the X-ray transmission image of the end product M. The determining part 12C determines, on the basis of the X-ray transmission image, whether there are areas whose brightness remarkably differs from that of the peripheral areas, and thereby determines whether the end product M is contaminated with foreign matter. Specifically, the determining part 12C retrieves the third threshold value (foreign matter detection threshold value) from the third storage part 13E, and, in cases where there are locations in the X-ray transmission image that exceed the third threshold value, determines that the end product M is contaminated with foreign matter.

Device Checking Part 12D

In the test mode, the device checking part 12D determines the test foreign matter P2 in the test piece P. In the test mode, a decision is made as to whether the detection value has exceeded the second threshold value retrieved from the second storage part 13D, in a prescribed range (portion corresponding to the test foreign matter P2) O, which is in a center portion of the coordinates of the annular marker P1 shown in FIG. 3, as recognized in the identification part 12B.

In the case that the number of pixels whose brightness value exceeds the second threshold value is within a prescribed range with regard to the range O of the center portion of the marker P1, the device checking part 12D determines that the X-ray inspection device 10 is in a normal state, wherein the test foreign matter P2 of the test piece P can be properly identified.

Conversely, in the case that the number of pixels whose brightness value exceeds the second threshold value is not within the prescribed range with regard to the range O, the device checking part 12D determines that the foreign matter inspection is not being properly carried out.

In cases where the X-ray inspection device 10 is determined to be functioning properly, on the basis of the determination results of the device checking part 12D, the controller 11 displays a message on the touch screen 26 indicating that the X-ray inspection device 10 is in a normal state. Conversely, in cases where the device checking part 12D determines that foreign matter inspection cannot be carried out properly, the controller 11 will display a message on the touch screen 26 indicating that the X-ray inspection device 10 is in an abnormal state, and therefore must be reconfigured.

Registration Part 12E

The registration part 12E stores the identification reference and the second threshold value in the first storage part 13C and the second storage part 13D, respectively, on the basis of the X-ray transmission image of the test piece P that was captured during the registration mode.

The operation of the system will be described below.

Registration Mode

First, the system is started, whereupon the operator carries out a prescribed operation using the touch screen 26 shown in FIG. 2A to set the CPU 12 to the registration mode. An image of the test piece P is then captured, and the captured X-ray transmission image is used as a basis to set the first threshold value and the shape of the marker P1 including the registered image for detecting the marker P1 shown in FIG. 3; and also to set the second threshold value for detecting the test foreign material P2. As a result of these settings being entered, the identification reference, which includes the first threshold value and the shape, will be stored in the first storage part 13C, and the second threshold value will be stored in the second storage part 13D.

Products M are then conveyed by the conveyor 50, and a third threshold value used by the X-ray inspection device 10 to inspect the products M for foreign matter is recorded in the third storage part 13E according to the property of the products M.

In the normal mode in which the products M are inspected, the test piece P is introduced at a suitable time, e.g., when the conveying (production) of the products M has paused.

The test piece P may be manually inserted by the operator. Alternatively, in cases where the products M are being conveyed at a high rate, the test piece P may be inserted between adjacent products M using a device 40 for inserting the test piece P, as shown in FIG. 2B.

The timing at which the test piece P is inserted may be set so that, e.g., if a combination weighing device 1 (FIG. 5) is present upstream of the X-ray inspection device 10, the test piece P will be inserted when any weights combined in the device 1 is not at a prescribed level, and therefore a space exists between the products M on the line for conveying the products M.

The X-ray image processing part 12A shown in FIG. 2A stores an X-ray transmission image (FIG. 3) in the temporary image storage part 13A on the basis of X-rays L that are received by the line sensor 22 (FIG. 1) at a prescribed timing.

The identification part 12B subsequently retrieves the identification reference from the first storage part 13C, and identifies whether the article in the X-ray transmission image is an end product M or a test piece P, based on the identification reference.

Specifically, the identification part 12B retrieves the first threshold value from the first storage part 13C, and determines whether the portions that exceed the first threshold value match the shape that is retrieved from the first storage part 13C.

When a marker P1 corresponding to the shape is determined to be present in the X-ray transmission image, the identification part 12B identifies the article as a test piece P, and sets the CPU 12 to the test mode.

Conversely, in cases where portions that exceed the first threshold value are not present, or in cases where the portions that exceed the first threshold value do not match the shape, the article is identified as an end product M, and the CPU 12 is set to the normal mode.

Normal Mode

When the CPU 12 is set to the normal mode, the determining part 12C retrieves the third threshold value from the third storage part 13E. When portions exceeding the third threshold value are not present in the X-ray transmission image of the end product M, the determining part 12C determines that the end product M to be an acceptable article that is not contaminated with foreign matter.

Conversely, when portions that exceed the third threshold value are present in the X-ray transmission image, the end product M is determined to be an unacceptable article that is contaminated with foreign matter. The determining part 12C transmits a sorting signal corresponding to the unacceptable product M to the sorting device 30 via the local control device 25, and stores the captured X-ray transmission image of the unacceptable product M in the NG image storage part 13B. Upon receiving the sorting signal, the sorting device 30 removes the unacceptable end product M corresponding to the sorting signal from the production line.

Test Mode

When the CPU 12 is set to the test mode, the device checking part 12D retrieves the second threshold value from the second storage part 13D. The device checking part 12D determines whether portions that exceed the second threshold value are present in the prescribed range O in the center portion of the annular marker P1 in the X-ray transmission image of the test piece P.

In a case where the number of pixels in the X-ray transmission image that exceed the second threshold value is within a prescribed range, the X-ray inspection device 10 is determined to be set normally In this case, the CPU 12 causes the touch screen 26 to display a message indicating that the X-ray inspection device 10 is operating normally.

Conversely, in a case where the number of pixels that exceed the second threshold value is out of the prescribed range, the CPU 12 causes the touch screen 26 to display a message indicating that an abnormal state is in effect, wherein the X-ray inspection device 10 cannot carry out normal foreign matter inspection; and that the X-ray inspection device 10 must be reconfigured or otherwise configured. The determining part 12C stores the X-ray transmission image of the test piece P in the NG image storage part 13B, and causes the sorting device 30 to remove the test piece P from the production line.

According to the X-ray inspection device of this embodiment, it is thus possible to identify the end product M from the test piece P using the identification part. Accordingly, the test piece P can be introduced without disrupting the flow of the end product M, thus making it possible to automatically shift to the test mode.

Therefore, in contrast to the prior art, the X-ray inspection device can be randomly checked, without temporarily halting the production line to switch the X-ray inspection device to a test mode. Consequently, inspections for foreign matter can be performed with dramatically higher reliability without reducing productivity.

Storing the X-ray transmission image of the test piece P in the NG image storage part 13B enables an inspection history to be retained for the X-ray inspection device 10. Consequently, it is possible to readily investigate the cause(s) underlying the rejected products M. The date and time at which the X-ray transmission image was captured may be stored associated with the image in the NG image storage part 13B.

Embodiment 2

Figure 5:
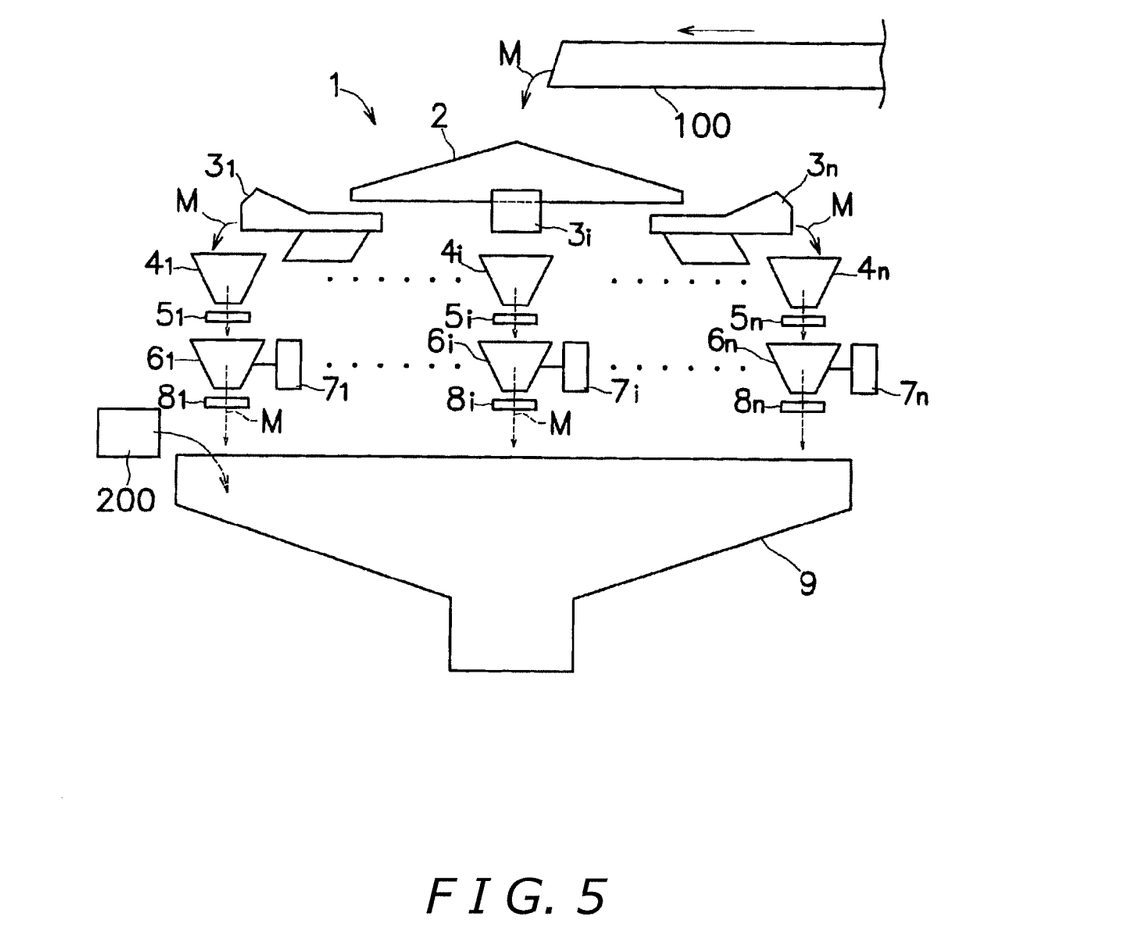
FIG. 5 is a schematic block diagram showing a combination weighing device provided with an inserting machine according to a section embodiment.

FIG. 5 shows Embodiment 2.

In Embodiment 2, a combination weighing device (example of a production machine) 1 includes an inserting machine 200 for randomly inserting a test piece P when so required.

A combination weighing device 1 will be briefly described below.

As shown in FIG. 5, a conveyor 100 dumps articles M, which are objects that are to be weighed, onto a distributing part 2. A small to large number of articles M are collected and sealed in bags for use as products.

Supply troughs 3i dump and supply the products M on the distributing part 2 to a plurality of pool hoppers 4i respectively, which are provided downstream from the supply troughs 3i respectively. Gates 5i are provided to the pool hoppers 4i respectively, and the articles M that are supplied and received from the supply troughs 3i are temporarily accommodated in the pool hoppers 4i. Weighing hoppers 6i are provided downstream from the pool hoppers 4i respectively. The weighing hopper 6i is provided with a gate 8i and a weighing head having a weight detector 7i. The weight detectors 7i detect the weight of the articles M introduced into the weighing hoppers 6i from the pool hoppers 4i respectively. A large collection chute 9 is provided beneath the gates 8i. The values for the weight of each of the articles M detected by the weight detectors 7i are combined, so that the sum of the combined values is or near a target value. The articles M corresponding to the combination are then grouped are dropped into, e.g., a bag making and packaging machine (not shown) located downstream of the device 1.

The inserting machine 200 discharges the test piece into the collection chute 9 when no combination-weighed articles are present, when a lot is being changed, or in another circumstance.

Having a test piece P introduced using a production machine located on an upstream side of the X-ray inspection device 10 thus makes it possible for products M, amongst which the test piece P has been interspersed, to be randomly sent through the X-ray inspection device.

A marker P1 is preferably formed in the test piece P so that a position of a test foreign matter P2 can be identified by the marker P1. For example, the markers P1 can be scattered so as to surround the test foreign matter P2, as shown in FIG. 4B. The markers P1 may also be arranged around the test foreign matter P2 in the form of straight lines arranged in a radial pattern, as shown in FIG. 4C. The coordinates of the range O of the center portion of the markers P1 in the X-ray transmission image are determined, e.g., by using the first threshold value as a reference, binarizing the image, and subsequently extracting the each of markers P1 in a rectangular form. The coordinates of the range O can be defined as the center of a graph including a number of markers P1.

Figure 4D:
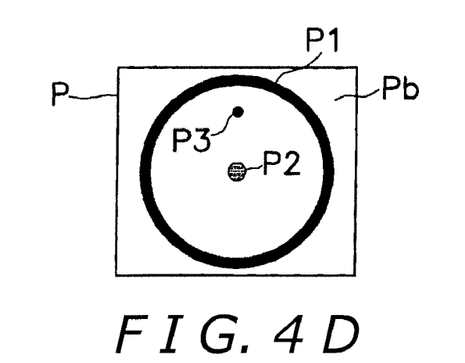
Figure 4E:
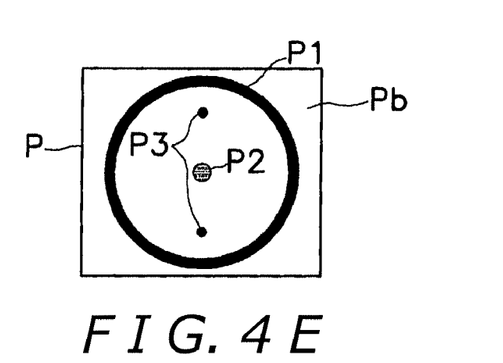

When a plurality of types of test foreign matter P2, P2 are required to be detected, a second marker P3 corresponding to the type of test foreign matter P2 may also be disposed in addition to the marker P1 for identifying the position of the test foreign matter P2, as shown in FIGS. 4D and E. The second marker P3 and the test foreign matter P2 corresponding to the second marker P3 are associated with one another and stored in the first storage part 13C.

Using a plurality of types of test foreign matter P2 thus makes it possible to confirm whether a plurality of types of foreign matter can be normally detected.

Preferred embodiments have been described above with reference to the drawings; however, a person skilled in the art could, on viewing the present specification, readily envision a variety of modifications within a self-evident scope.

For example, two X-ray sources and two line sensors may be provided, two mutually different cross-sections may be inspected, and the accuracy of the inspection can be improved.

Consequently, such modifications can be construed as lying within the scope of the present invention as set forth in the claims.

The invention claimed is:

1. An X-ray inspection device for irradiating an article with X-rays and inspecting the article while the article is being conveyed, the X-ray inspection device comprising:
    a conveying unit configured and arranged to convey the article;
    an identification part configured and arranged to identify whether the article is a test piece or an end product by determining whether a transmission image of the X-rays irradiated onto the article includes a pattern corresponding to a prescribed identification reference for identifying the test piece; and
    an operation control part configured to set operation of the X-ray inspection device to a normal mode in which the article is determined to be defective or not defective when the article has been identified as an end product by the identification part, and to a test mode in which a state of the X-ray inspection device is assessed by comparing a prescribed portion of the transmission image of the X-rays corresponding to a test foreign matter with a threshold value when the article has been identified as a test piece by the identification part.

2. The X-ray inspection device as recited in claim 1, further comprising
    a first storage part configured and arranged to store the prescribed identification reference.

3. The X-ray inspection device as recited in claim 2, further comprising
    a registration part configured and arranged to execute a registration mode in which the prescribed identification reference is obtained from a reference transmission image of the X-rays with which a test piece is irradiated.

4. The X-ray inspection device as recited in claim 3, further comprising a second storage part configured and arranged to store the threshold value corresponding to the test foreign matter provided to the test piece in the registration mode.

5. The X-ray inspection device as recited in claim 1, wherein the identification part is configured and arranged to identify whether the article is a test piece or an end product based on a timing at which the article is conveyed.

6. A production system comprising the X-ray inspection device as recited in claim 1, and a production machine disposed on an upstream side of the X-ray inspection device, wherein the test piece is introduced in the production machine.

* * * * *